(12) United States Patent
Smith et al.

(10) Patent No.: US 7,727,248 B2
(45) Date of Patent: Jun. 1, 2010

(54) SURGICAL CLIP

(75) Inventors: Kevin W. Smith, Coral Gables, FL (US); Jose Luis Francese, Miami Springs, FL (US); Robert Sixto, Jr., Miami, FL (US); Juergen A. Kortenbach, Miami Springs, FL (US); Thomas O. Bales, Coral Gables, FL (US); Carlos Rivera, Cooper City, FL (US); Matthew A. Palmer, Miami, FL (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1752 days.

(21) Appl. No.: 10/867,412

(22) Filed: Jun. 14, 2004

(65) Prior Publication Data
US 2005/0033333 A1 Feb. 10, 2005

Related U.S. Application Data

(63) Continuation-in-part of application No. 10/730,236, filed on Dec. 8, 2003, which is a continuation of application No. 09/891,775, filed on Jun. 25, 2001, now Pat. No. 6,716,226.

(51) Int. Cl.
*A61B 17/08* (2006.01)
(52) U.S. Cl. .......................... 606/158; 24/543
(58) Field of Classification Search ................ 606/142, 606/143, 151, 157, 158; 24/543
See application file for complete search history.

(56) References Cited

U.S. PATENT DOCUMENTS

| 266,632 | A | | 12/1882 | Danforth | |
|---|---|---|---|---|---|
| 4,444,187 | A | | 4/1984 | Perlin | 128/346 |
| 4,492,232 | A | * | 1/1985 | Green | 606/143 |
| 4,512,345 | A | * | 4/1985 | Green | 606/143 |
| 4,556,058 | A | * | 12/1985 | Green | 606/143 |
| 4,648,158 | A | * | 3/1987 | West | 24/23 W |
| 4,800,879 | A | * | 1/1989 | Golyakhovsky et al. | 606/158 |
| 4,934,364 | A | * | 6/1990 | Green | 606/143 |
| 5,312,426 | A | | 5/1994 | Segawa | 606/158 |
| 5,330,442 | A | * | 7/1994 | Green et al. | 606/232 |
| 5,354,306 | A | | 10/1994 | Garvey, III | 606/157 |
| 5,366,459 | A | | 11/1994 | Yoon | 606/151 |
| 5,376,101 | A | * | 12/1994 | Green et al. | 606/232 |
| 5,425,740 | A | | 6/1995 | Hutchinson | 606/157 |
| 5,441,509 | A | | 8/1995 | Vidal et al. | 606/151 |
| 5,464,416 | A | | 11/1995 | Steckel | 606/158 |
| 5,487,746 | A | | 1/1996 | Yu et al. | 606/151 |
| 5,522,823 | A | | 6/1996 | Kuntz et al. | 606/157 |

(Continued)

*Primary Examiner*—Todd E Manahan
*Assistant Examiner*—E. B.
(74) *Attorney, Agent, or Firm*—Gordon & Jacobson, PC

(57) ABSTRACT

A surgical clip has a base portion and two generally parallel, spaced arms extending from the base portion and defining an opening therebetween. The arms terminate distally in fingers which are of reduced width and thickness relative to the arms and which are adapted to be bent towards and past each other. A transition section from each arm to the finger provides curved structures which extending away from each other and providing a wider mouth for the opening between the arms. The arms also have a proximal section with an undercut which helps in flexure of the arms. The base is an extended structure having a rounded proximal end with outwardly extending shoulders which are arranged to be engaged by the curved structures of the mouth of another clip.

16 Claims, 8 Drawing Sheets

U.S. PATENT DOCUMENTS

| | | |
|---|---|---|
| 5,632,753 A | 5/1997 | Loeser .................. 606/151 |
| 5,741,283 A | 4/1998 | Fahy .................... 606/157 |
| 5,993,476 A | 11/1999 | Groiso .................. 606/219 |
| 6,015,417 A * | 1/2000 | Reynolds, Jr. .......... 606/151 |
| 6,716,226 B2 | 4/2004 | Sixto, Jr. et al. ...... 606/157 |
| 2002/0198549 A1 | 12/2002 | Sixto et al. |

* cited by examiner

SURGICAL CLIP

This application is a continuation-in-part of U.S. Ser. No. 10/730,236, hereby incorporated by reference herein in its entirety, which is a continuation of U.S. Ser. No. 09/891,775, filed Jun. 25, 2001, now issued as U.S. Pat. No. 6,716,226. This application is also related to U.S. Ser. No. 10/867,501 entitled "Endoscopic Surgical Instrument Having a Force Limiting Actuator" and filed on even date herewith, which is hereby incorporated by reference herein in its entirety.

BACKGROUND OF THE INVENTION

1. Field of the Invention

This invention relates broadly to surgical devices. More particularly, this invention relates to a surgical clip for clamping and/or suturing ducts, vessels, and other tissues, or for anchoring a tissue, or for attaching a foreign body to a tissue.

2. State of the Art

Surgical clips are generally used to apply clamping force to ducts, vessels, and other tissues. In addition, surgical clips are particularly useful in controlling bleeding of a tissue in lieu of suturing or stapling where suturing or stapling is difficult. However, in certain circumstances, the bleeding tissue is lubricous, and applied clips often slip from the tissue and are dislodged, removing the necessary clamping force thereabout. This is particularly a problem when a clip is provided about tissue which is not a conduit of a size which can be completely surrounded by the clip. For example, it is very difficult to secure a clip about a small peripheral portion of ulcerated stomach tissue and therefore it is difficult to effect hemostasis of such bleeding tissue with a clip. Moreover, the problem is amplified when the clip used is very small.

In order to prevent dislodgement, a combination of a clip and a staple has been described in U.S. Pat. No. 5,522,823 to Kuntz et al. In the Kuntz clip, one end portion of the clip is pierced through the tissue and captured in an eye of another end portion of the clip to secure the clip on the tissue. With the clip piercing the tissue, the likelihood that the clip will become inadvertently dislodged is greatly reduced.

While the Kuntz et al. clip represents a step forward, the disclosed clip is not particularly useful in endoscopic procedures. In particular, both the nature of the clip and the manner in which it is applied are complex. For example, in order to facilitate the bending of the clip through various configurations required of its applier, the clip has portions provided with at least four different widths as well as an eye opening. This complex clip structure is not practical for a clip which is to be used in a flexible endoscopy procedure in which the tools used are of very small diameter, e.g., 2-6 mm (0.08-0.24 inch). In addition, for endoscopic procedures it is highly desirable that multiple clips be able to be applied without removing the clip applier from its general location. The Kuntz et al. clip and applier, however, are not particularly adapted for applying multiple clips, as the Kuntz et al. clip does not stack, and the applier with which it is used holds a single clip at a time.

The problems of the Kuntz et al. clip were overcome with the clip described in the parent application hereto. That surgical clip was provided with a generally U-shaped configuration with first and second arms, and a bridge portion therebetween. The first arm was provided with a tip preferably having one or more catches, and the second arm extended into a deformable retainer preferably having a tissue-piercing end and preferably also a hook. During application, the clip was forced over compressed tissue. As the clip was forced over the tissue, the retainer of the second arm was bent and could pierce through the tissue. The retainer was sized to be bent sufficiently toward and around the tip of the first arm so that the hook could engage in one of the catches to secure the clip to the tissue and prevent the clip and tissue from separating. The clip was provided with structure that facilitated the stacking (or chaining) of a plurality of clips in a clip chamber of an applier. The structure included: a notch at a junction of the first arm and the bridge portion adapted to receive the tip of the first arm of another clip; an elongate recess along the exterior of the second arm adapted to receive the retainer of the second arm of another clip; and an interior configuration at the ends of the first and second arms corresponding to an exterior portion of the bridge portion of another clip.

While the clip of the parent application overcame the problems of the prior art, it was found that in certain circumstances, the tip of one arm of the clip did not engage the catch on the other arm. In addition, it was found that to effectively dispense the clip, it was preferable that the clip applier include a mechanism which pulled the penultimate (next) clip proximally after the ultimate clip was dispensed in order to ready the clip applier for use again in firing the next clip. Therefore, it was determined that further improvements to the clip could be made.

SUMMARY OF THE INVENTION

It is therefore an object of the invention to provide a surgical clip which remains secured to the tissue to which it is applied.

It is another object of the invention to provide a surgical clip which pierces tissue in order to maintain a secure hold on the tissue to which it is applied.

It is a further object of the invention to provide a surgical clip which is adapted for use in minimally invasive surgery.

It is an additional object of the invention to provide a surgical clip which can be applied in a flexible endoscopy setting.

It is also an object of the invention to provide a surgical clip which can be used with rigid instruments operated through a port in the human body.

An additional object of the invention is to provide a surgical clip which is relatively easy to manufacture.

A further object of the invention is to provide a surgical clip which is particularly adapted for use in an applier which holds a plurality of clips.

Another object of the invention is to provide a surgical clip which can stack in an axial manner, but which does not require proximal movement of a penultimate clip after firing of the ultimate clip.

In accord with these objects, which will be discussed in detail below, a surgical clip is provided having a base portion and two generally parallel, spaced arms extending from the base portion and defining an opening therebetween. The arms terminate distally in fingers which are of reduced width and thickness relative to the arms and which are adapted to be bent towards and past each other. A transition section from each arm to the finger provides curved structures, with the curved structures extending away from each other and providing a wider mouth for the opening between the arms. The arms also have a proximal section with an undercut (reduced height section) which help in flexure of the arms. According to a preferred aspect of the invention, the base is an extended structure having a rounded proximal end with outwardly extending shoulders which are arranged to be engaged by the curved structures of the mouth of another clip. From the shoulders, the base narrows as it extends toward a bridge portion which bridges the arms. At the bridge, the arms are of full thickness and each includes a rearwardly extending fin which overlies the base. The area between the fin and the base provides a protective undercut in which the tips of the fingers of another clip may be protected.

It will be appreciated that when a plurality of clips of the invention are stacked axially (linearly), the stack may be advanced by pushing a proximal clip, as the mouth of each clip will push on the shoulders of the base of a forwardly-adjacent clip. As the stack is advanced, the fingers of a rearwardly-adjacent clip are not endangered as the fingers do not engage the base and do not do the pushing.

It will also be appreciated that as the stack of clips is advanced, the distal-most (ultimate) clip will be moved into the jaws of the clip applier and over the tissue to be clipped. Full movement of the clip will result in the arms of the clip being formed against an anvil of the clip applier such that the arms are bent preferably through at least ninety degrees, and up to one hundred eighty-degrees; i.e., preferably at least to each other and typically past each other.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
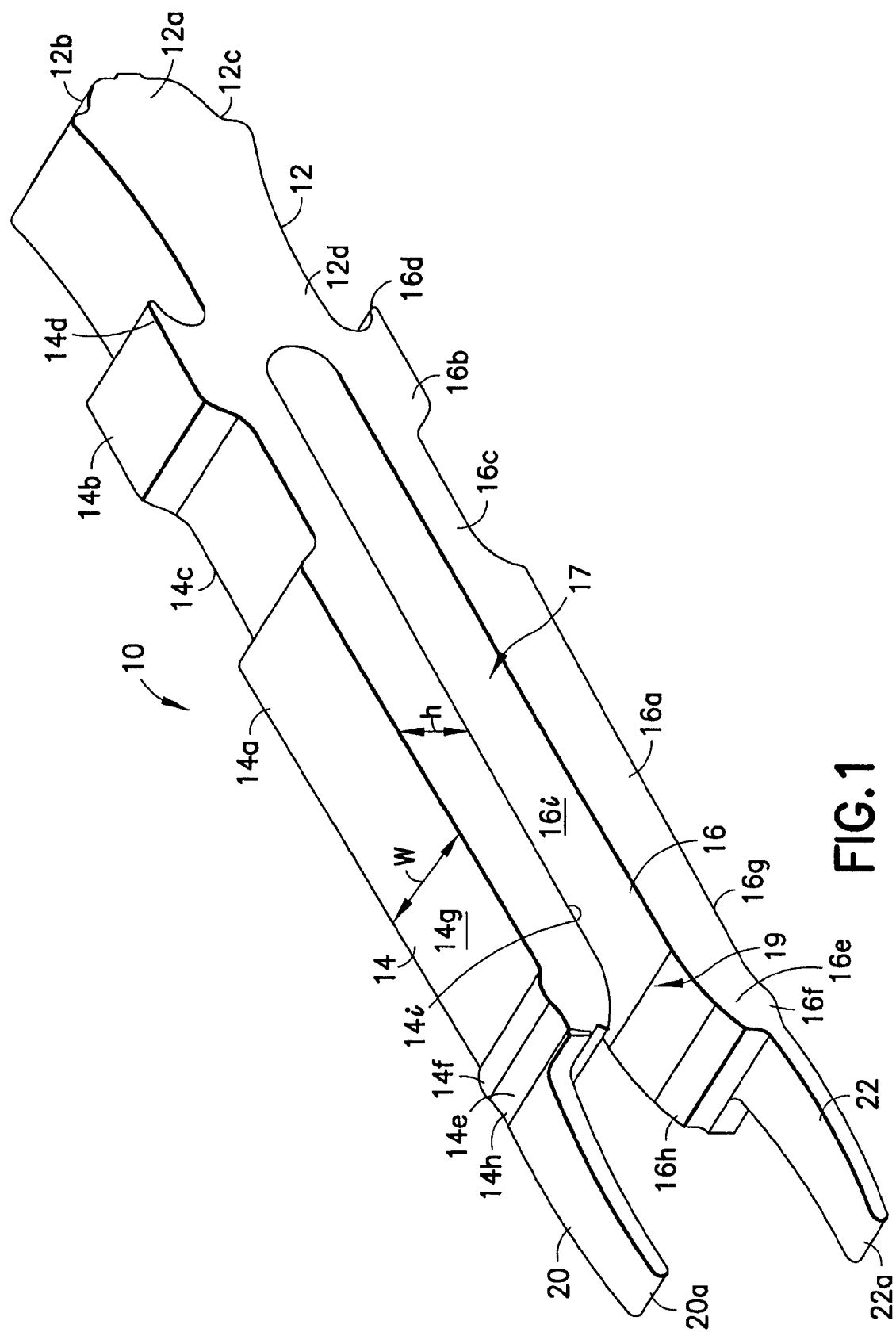
FIG. 1 is a perspective view of the clip of the invention.
Figure 2:
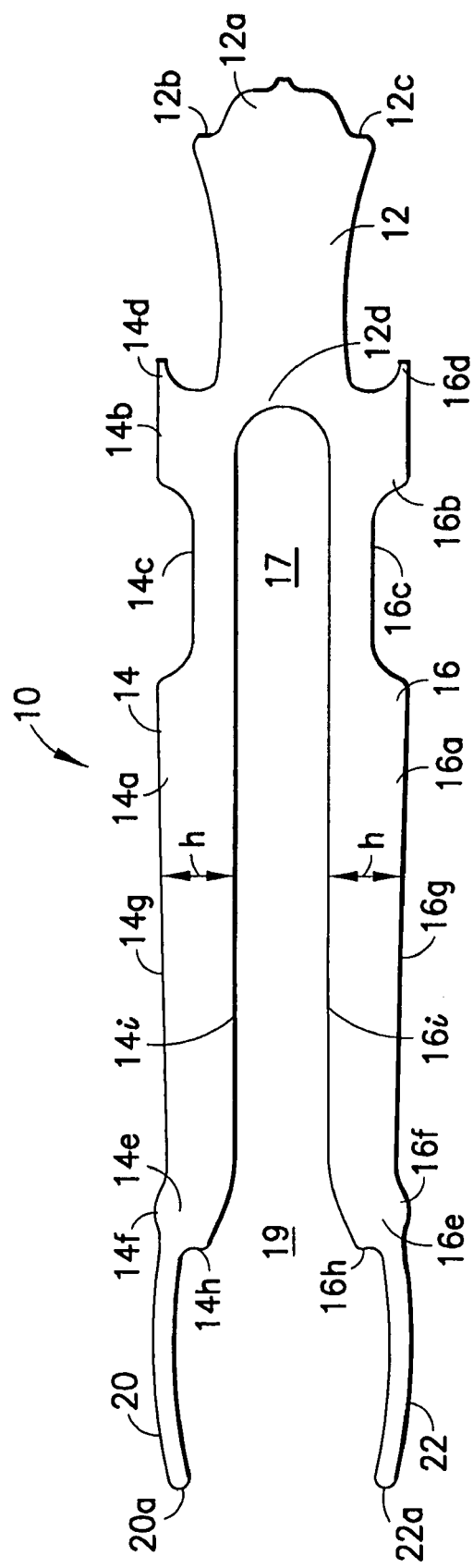
FIG. 2 is a side view of the clip of FIG. 1.
Figure 3:
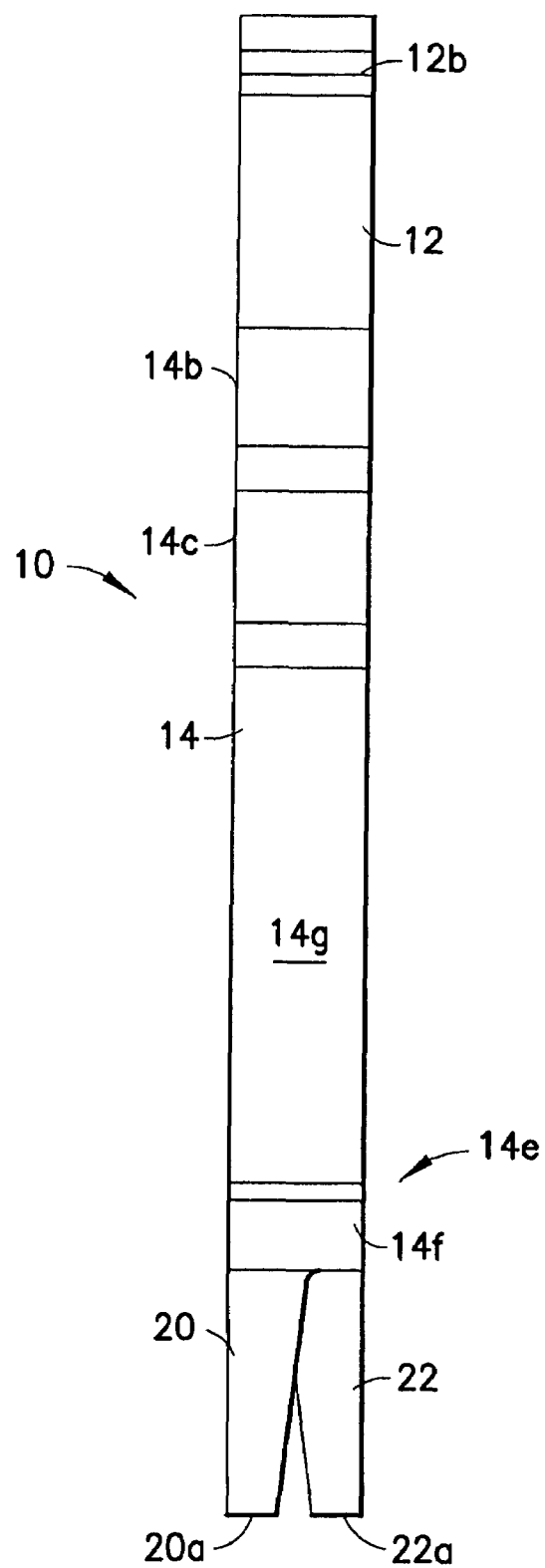
FIG. 3 is a top view of the clip of FIG. 1.

Turning now to FIGS. 1-3, a first embodiment of a surgical clip 10 according to the invention is seen. The surgical clip 10 is shown having an extended base portion 12 and two generally parallel, spaced arms 14, 16 extending from the base portion 12 and defining an opening 17 therebetween. The arms 14, 16 terminate distally in fingers or tines 20, 22.

Figure 4:
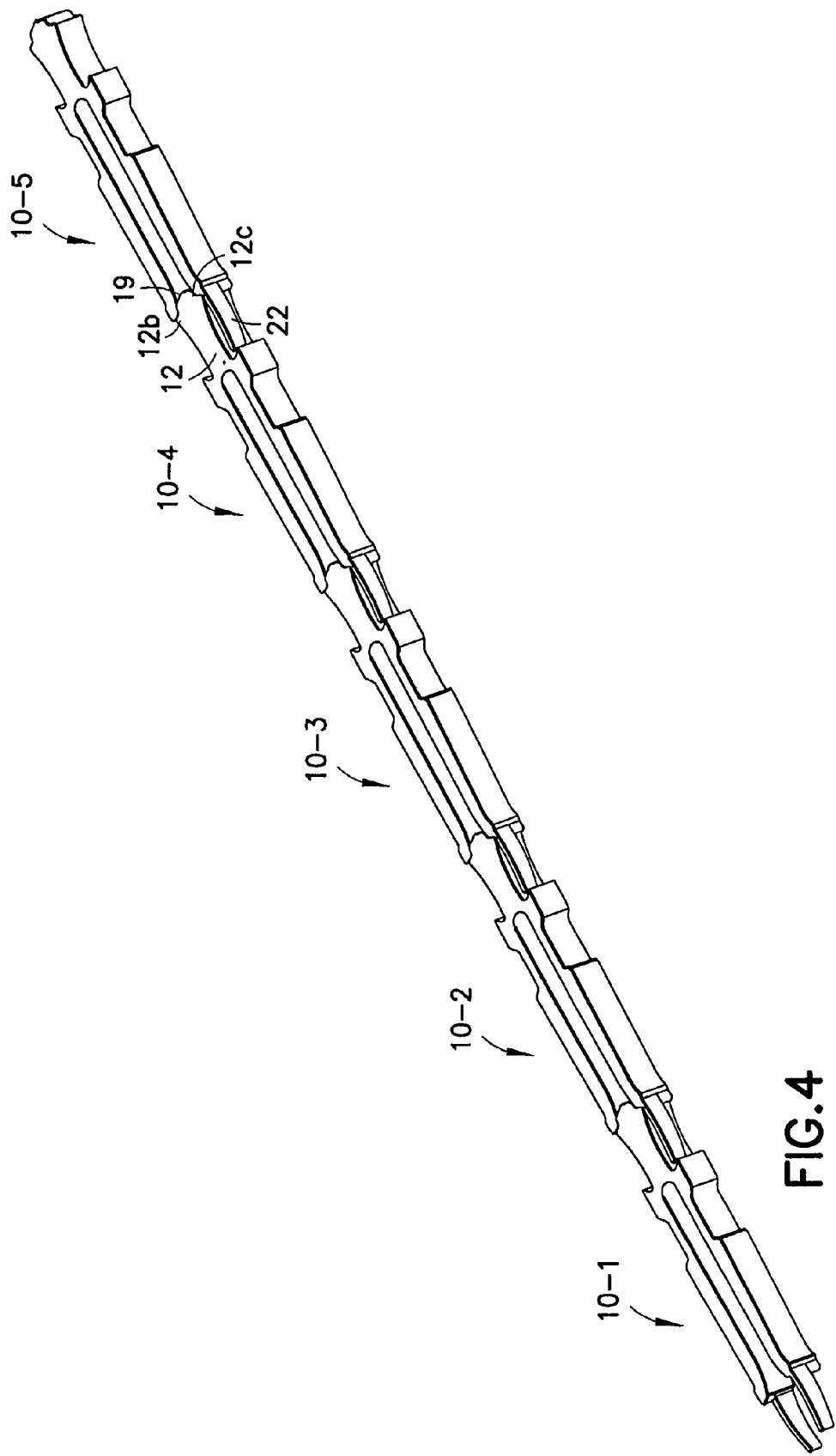
FIG. 4 is a perspective view of a train of clips of the invention.

As seen best in FIG. 1, the arms 14, 16 have a generally uniform width w, and also have a generally uniform height h along a main portion 14a, 16a, of the arm, although the arms do taper down in height slightly as they extend distally. Between a very proximal portion of the arms 14b, 16b, and the main portions 14a, 16a, an undercut (reduced height) section 14c, 16c is provided which helps in permitting the arms to flex as will be discussed hereinafter. The proximal portions 14b, 16b of the arms include a rearwardly extending fin 14d, 16d which overlie the base 12. The area between the fin and the base provides a protective undercut in which the tips of the fingers of another clip may be protected (as seen in FIG. 4). The distal portions of the arms provide a transition section 14e, 16e from each arm to its associated finger. The transition section is somewhat oval in shape. In particular, the arms at the transition sections 14e, 16e, first increase in height with bumps 14f, 16f on the surfaces 14g, 16g of the arms which face away from each other (for purposes of alignment with a clevis of the clip applier—not shown), and then decrease in height at pushing portions 14h, 16h as they transition toward the fingers 20, 22. At should be appreciated that at the transition sections 14e, 16e, the surfaces 14i, 16i of the arms which face each other diverge from each other. This divergence provides a wider mouth area 19 which leads into the opening 17.

The fingers 20, 22 of the clip are seen to be of substantially reduced width and thickness relative to the arms. In the embodiment of FIGS. 1-3, the fingers 20, 22 are approximately ⅓ the thickness (height) of the arms and terminate in rounded tips 20a, 22a, although if desired, the tips could be sharp. The fingers also taper in width (i.e., they are angle cut) as they extend distally toward their free ends, and are designed such that the sum of the width at their tips plus the width at their bases (where they are attached to the transition sections 14h, 16h of the arms) are preferably slightly less than, but at most, equals the width of the arms. With this arrangement, and as seen best in FIG. 3, the width of the fingers at the mid-section of the fingers is approximately ½ the width of the arms; and with this arrangement, it is possible for each of the fingers to be bent by 180 degrees past the other finger. If desired, the fingers can be slightly arced (as shown in FIGS. 1, 2, and 4), or they can be flat. It will be appreciated by those skilled in the art that by providing an arc, the amount of force required to form (buckle) the clip is lowered, and the direction of buckling and the final shape of the clip are dictated.

According to a preferred aspect of the invention, and as seen best in FIG. 2, the base 12 is an extended structure having a rounded crown-shaped proximal end 12a with outwardly extending shoulders 12b, 12c. From shoulders 12b, 12c, the base tapers down in height slightly as it extends toward a bridge portion 12d of the base which bridges the arms 14, 16. The length of the base 12 is preferably similar to the length of the fingers 20, 22. As mentioned previously, the areas between the bridge 12d of the base 12 and the fins 14d, 16d of the arms provide protective undercuts in which the tips of the fingers of another clip may be protected (as seen in FIG. 4).

Turning now to FIG. 4, it will be appreciated that when a plurality of clips (e.g., 10-1, 10-2, 10-3, 10-4, and 10-5) of the invention are stacked axially (linearly), the stack may be advanced by pushing a proximal clip, as the shoulders 12b, 12c of each forwardly-adjacent clip will be received in the mouth 19 of each rearwardly-adjacent clip (i.e., pushed by the inner surfaces 14i, 16i of the pushing sections 14h, 16h) (FIG. 2). As the stack is advanced, the fingers 20, 22 of a rearwardly-adjacent clip are not endangered as the fingers do not engage the base 12 and do not do the pushing.

It will also be appreciated that as the stack of clips is advanced, the distal-most (ultimate) clip will be moved into the jaws of the clip applier (not shown) and over the tissue to be clipped (not shown). Because the mouth 19 defined by the transition sections 14e, 16e is wider than the opening 17, the clip can readily extend over tissue, even if the tissue is slightly thicker than the opening 17. In such cases, as the clip is moved over the tissue, the arms 14, 16 can flex outwardly and provide compression to the tissue, with the undercuts 14c, 16c providing additional flexibility to the arms.

Figure 5:
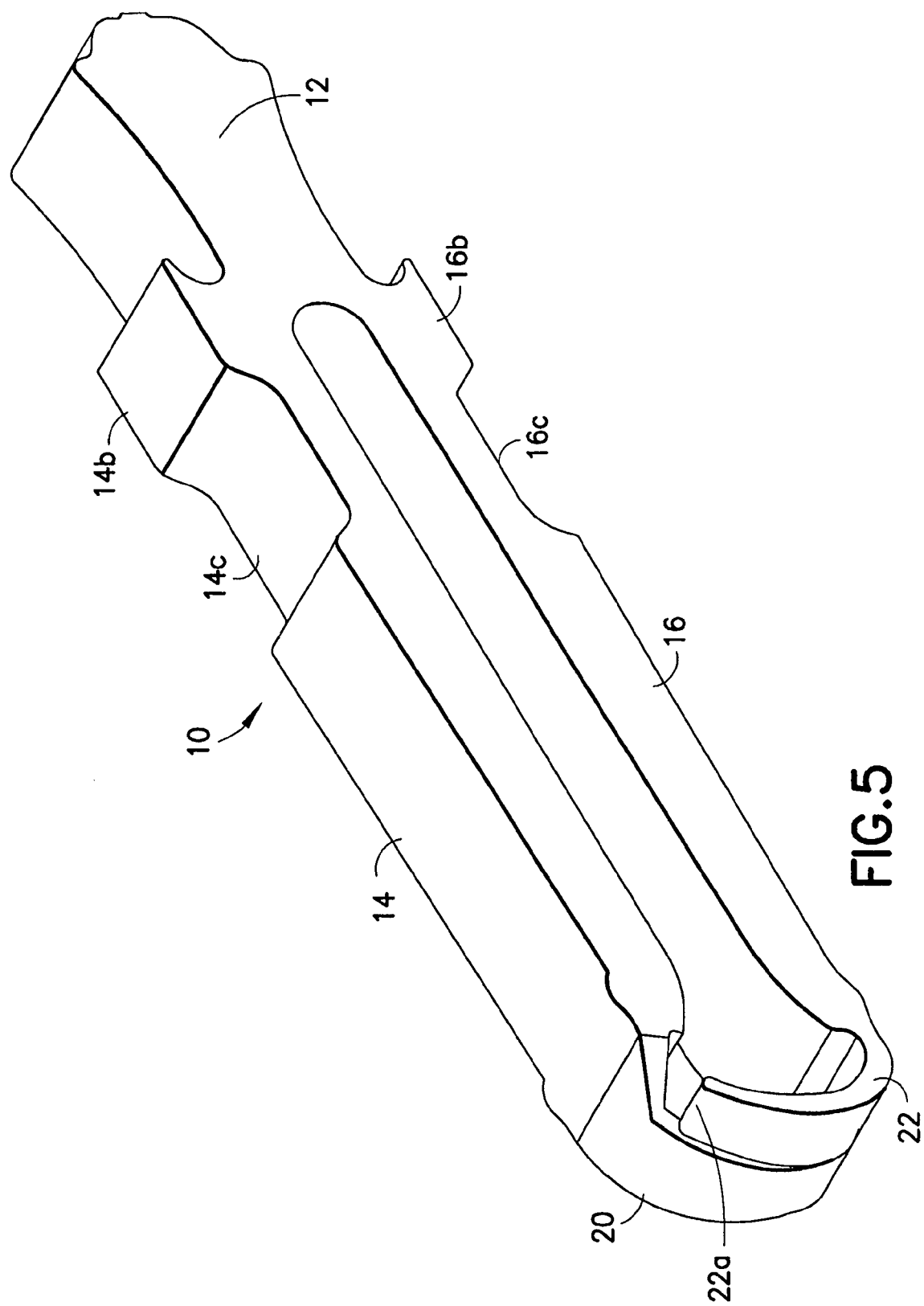
FIG. 5 is perspective view of a clip of the invention after forming.

As discussed in the co-filed previously incorporated U.S. Ser. No. 10/867,501, the clip 10 is designed such that as the clip is moved over the tissue, the fingers 20, 22 are formed against an anvil of the substantially closed jaws of a clip applier (not shown). As the fingers hit the anvil, the arms are bent preferably through at least ninety degrees, and up to one hundred eighty-degrees; i.e., preferably at least to each other and typically past each other. The fingers are formed such that they will typically contact each other as they extend to and past each other. A clip formed in this manner is seen in FIG. 5. Thus, according to a method of the invention, the clip of the invention is applied over tissue and forced forward such that the fingers of the clip are bent through at least ninety degrees and up to one hundred eighty-degrees around or through tissue.

According to the presently preferred embodiment of the invention, the clip 10 of FIGS. 1-4 is made out of titanium. The size of the clip will depend upon its application. By way of example only, for upper gastrointestinal hemostasis applications, the length of the clip is preferably between 5 mm and 9 mm, the width of the clip is preferably between 0.5 mm and 1.5 mm, and the overall height of the clip is between 1 mm and 2 mm, with each arm having a characteristic height of between 0.3 mm and 0.7 mm. The length of the fingers is preferably between 1 mm and 2 mm, and the length of the base is preferably between 1 mm and 3 mm.

Also, according to the presently preferred embodiment of the invention, the clip 10 is symmetrical about a longitudinal axis running through the base and between the arms; i.e., the clip may be rotated one hundred-eighty degrees about the axis and the resulting configuration will be the same. Thus, the clip may be stacked with other clips without concern for its orientation.

Figure 6:
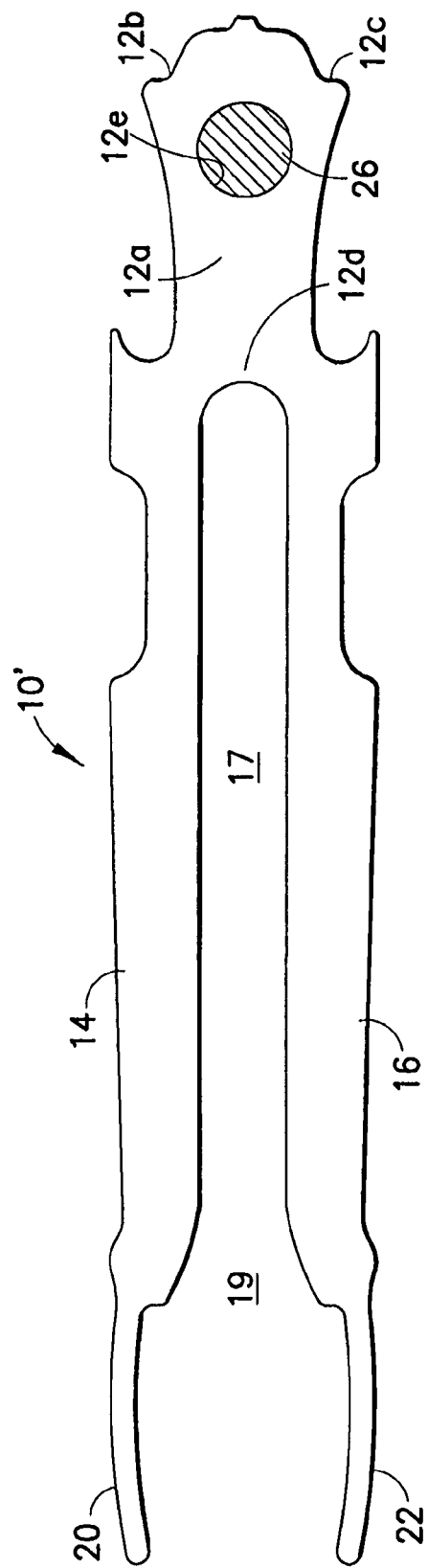
FIG. 6 is a side view of a second embodiment of the clip of the invention having a modified base.

A second embodiment of the clip of the invention is seen in FIG. 6. The clip 10' is identical to the clip 10 of FIGS. 1-3, except that a hole is provided in the base 12. The hole 12e can extend partially (i.e., as a "blind hole") or completely through the base and is adapted to receive a marker 26. The marker 26 can be radiographic, MRI-visible, or otherwise visible as desired. Alternatively, the hole can be used to receive a suture. Where a train of clips 10' are provided, a single suture can be used to run through the holes of all of the clips in the train such that the clips can be cinched together after they are dispensed.

Figure 7:
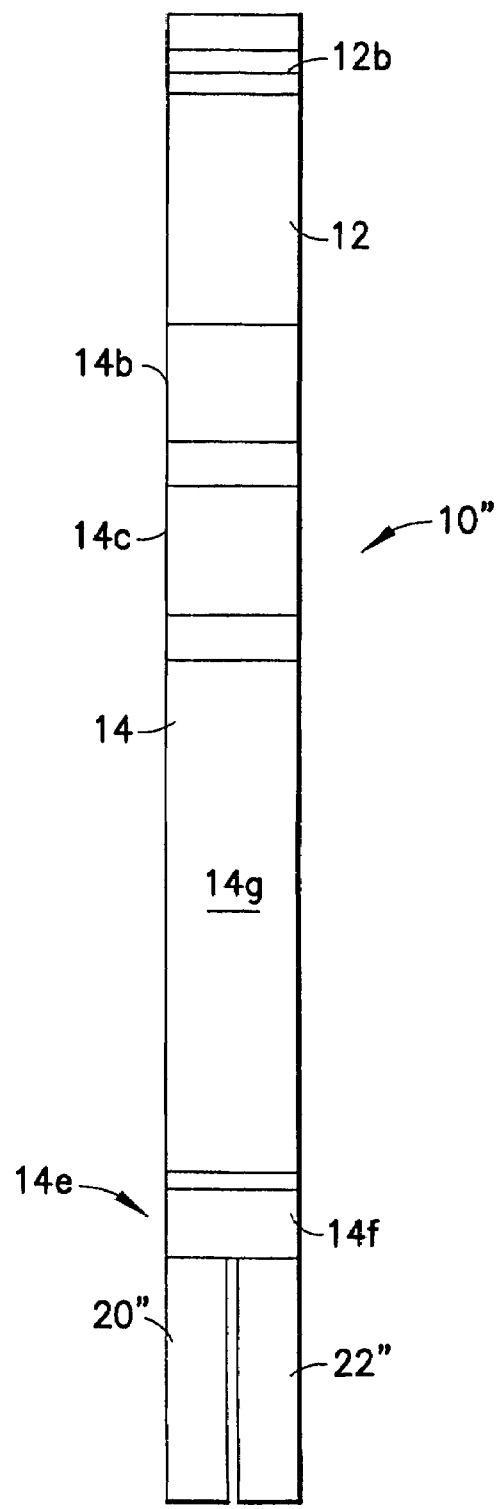
FIG. 7 is a top view of a third embodiment of the clip of the invention having modified fingers.

A third embodiment of the clip of the invention is seen in FIG. 7. Clip 10" is identical to clip 10 of FIGS. 1-3 except that the fingers 20", 22" do not taper in width (i.e., they are straight). The width of each finger 20", 22" is chosen to be approximately ½ the width of the arms.

Figure 8:
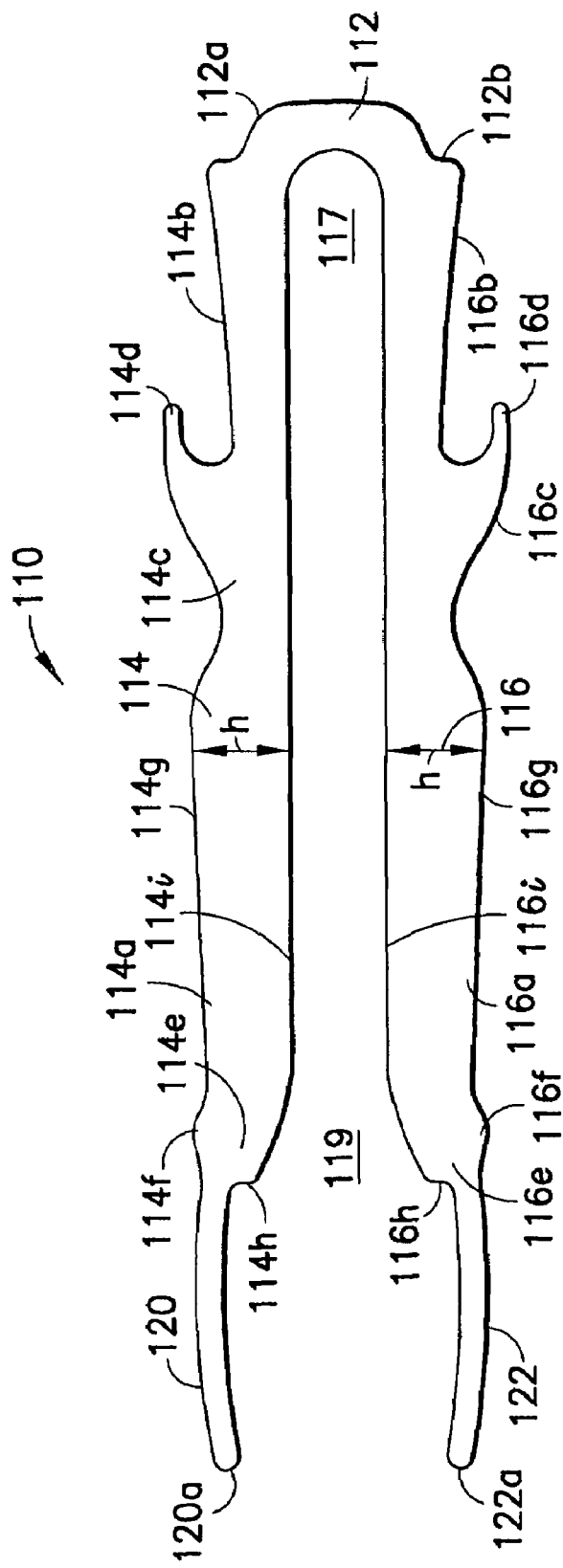
FIG. 8 is a side view of a fourth embodiment of the clip invention with a bridge section having shoulders.

A fourth (less preferred) embodiment of a surgical clip 110 is seen in FIG. 8. The surgical clip 110 includes a base or bridge 112 and two generally parallel, spaced arms 114, 116 extending from the bridge 112 and defining an opening 117 therebetween. The arms 114, 116 terminate distally in fingers or tines 120, 122. The arms 114, 116 have a generally uniform width, and also have a generally uniform height h along a main portion 114a, 116a, of the arm, although the arms do taper down in height slightly as they extend distally. The arms also include proximal portions 114b, 116b which are sized to be about the same length as fingers 120, 122. Between the proximal portion of the arms 114b, 116b, and the main portions 114a, 116a, the arms 114, 116 are provided with an undercut (reduced height) section 114c, 116c which helps in permitting the arms to flex, and an optional rearwardly extending fin 114d, 116d which overlies the proximal portion of the arms 114b, 116b. The areas between the fins and the proximal portions of the arms provides protective undercuts in which the tips of the fingers of another clip may be protected. The distal portions of the arms provide a transition section 114e, 116e from each arm to its associated finger. The transition section is somewhat oval in shape. In particular, the arms at the transition sections 114e, 116e, first increase in height with bumps 114f, 116f on the surfaces 114g, 116g of the arms which face away from each other (for purposes of alignment with a clevis of the clip applier—not shown), and then decrease in height at pushing portions 114h, 116h as they transition toward the fingers 120, 122. At should be appreciated that at the transition sections 114e, 116e, the surfaces 114i, 116i of the arms which face each other diverge from each other. This divergence provides a wider mouth area 119 which leads into the opening 117.

The fingers 120, 122 of the clip are of substantially reduced width and thickness relative to the arms. In the embodiment of FIG. 8, the fingers 120, 122 are approximately ⅓ the thickness (height) of the arms and terminate in rounded tips 120a, 122a, although if desired, the tips could be sharp. The fingers also taper in width (i.e., they are angle cut) as they extend distally toward their free ends, and are designed such that the sum of the width at their tips plus the width at their bases (where they are attached to the transition sections 114h, 116h of the arms) are preferably slightly less than, but at most, equals the width of the arms.

In the embodiment of FIG. 8, the bridge 112 is not an extended structure although it has a rounded crown-shape. The bridge is provided with outwardly extending shoulders 112a, 112b which are sized to be engaged by pushing portions 114h, 116h of another clip 110.

According to another aspect of the invention, the clips of the invention may be color coded. In one embodiment, the clips are colored based on the procedure with which the clip is to be used; e.g., red for marking; green for attachment of feeding tubes; blue for hemostasis, yellow for tissue approximation, black for the upper gastrointestinal tract, cyan for the lower gastrointestinal tract, etc. According to another embodiment, each clip in a train is provided with a different color, so that the practitioner will know which clip is being dispensed and how many clips are left for dispensing. For example, if seven or fewer clips are used, they may be provided with rainbow colors in the known order: red, orange, yellow, green, blue . . . , so that the practitioner will always know that the red clip was dispensed first, the orange next, etc. (or in the reverse order). According to yet another embodiment, only the last (most proximal) clip or the penultimate clip in the train may be colored with a color different than the other clips. In this manner, the practitioner will know that the last, or next-to-last clip has been dispensed. Thus, with color-coded clips, the method of the invention includes viewing the dispensed clip as it is dispensed or after it is dispensed, determining the color of that clip, and making a determination relative to a clip applier (e.g., whether to remove the clip applier from the surgical site, or to locate the clip applier where a "last" clip is to be applied before removing the clip applier from the surgical site) based on the color of the clip.

There have been described and illustrated herein several embodiments of a surgical clip and a method of applying the surgical clips to tissue. While particular embodiments of the invention have been described, it is not intended that the invention be limited thereto, as it is intended that the invention be as broad in scope as the art will allow and that the specification be read likewise. Thus, while particular sizes of clips have been disclosed, it will be appreciated that other sizes could be used as well. In addition, while particular materials have been disclosed, it will be understood that other materials can be used. Further, while the fingers of the clips were described as having a thickness or height approximately one-third the height of the arms, it will be appreciated that fingers of thicknesses of one-half the height of the arms or more could be utilized, or thicknesses less than one-third the height could be utilized. It will therefore be appreciated by those skilled in the art that yet other modifications could be made to the provided invention without deviating from its spirit and scope as claimed.

What is claimed is:

1. A surgical clip, comprising:
   a) a base having spaced engagement shoulders and a bridge portion, said spaced engagement shoulders being proximal to said bridge portion;
   b) two spaced arms extending distally from said base and defining an opening therebetween, said spaced arms having a first width at midportions of said arms, each of said arms including a proximal portion adjacent said bridge portion, each of said proximal portions including a rearwardly extending fin spaced from said base; and
   c) two fingers extending respectively from said spaced arms, said fingers being of reduced width relative to said first width, and said fingers being offset from each other relative to a longitudinal axis which extends through said base and between said arms, said fingers in a first pre-formed condition extending in a substantially straight line and substantially parallel to each other and in a second installed position said fingers curving through an arc of at least 90°,
   wherein each said spaced arm includes a transition section adjacent a said respective finger, said transition sections of said spaced arms having surfaces spaced from and facing each other, said surfaces of said transitions sections and said engagement shoulders being sized and shaped to engage each other.

2. A surgical clip according to claim 1, wherein:
said arms have a first height at midportions of said arms, and said fingers are of reduced height relative to said first height.

3. A surgical clip according to claim 2, wherein:
said reduced height is less than one-half said first height.

4. A surgical clip according to claim 1, wherein:
said surgical clip is symmetrical about said longitudinal axis.

5. A surgical clip according to claim 1, wherein:
said base has a first length, and said fingers have second lengths similar to said first length.

6. A surgical clip according to claim 5, wherein:
said fingers are spaced sufficiently apart from each other such that, were said surfaces of said transitions sections to engage said engagement shoulders, said fingers would not engage said base.

7. A surgical clip according to claim 1, wherein:
said arms have a first height at midportions of said arms, and each said arm include an undercut portion proximal said midportion, said undercut portion having a reduced height relative to said first height.

8. A surgical clip according to claim 1, wherein:
said fingers taper down in width as they extend away from said arms.

9. A surgical clip according to claim 8, wherein:
a sum of a width of a said finger at a distal tip of said finger plus a width of said finger adjacent said transition section substantially equals said first width.

10. A surgical clip according to claim 1, wherein:
said fingers are arced.

11. A surgical clip according to claim 1, wherein:
each said transition section includes a section of increased height relative to an adjacent portion of the arm of said transition section.

12. A surgical clip according to claim 1, wherein:
said surfaces of said transition sections diverge from each other and define a mouth which is wider than said opening.

13. A surgical clip, comprising:
   a) a base having spaced engagement shoulders and defining a hole;
   b) two spaced arms extending distally from said base and defining an opening therebetween, said spaced arms having a first width at midportions of said arms;
   c) two fingers extending respectively from said spaced arms, said fingers being of reduced width relative to said first width, and said fingers being offset from each other relative to a longitudinal axis which extends through said base and between said arms, said fingers in a first pre-formed condition extending in a substantially straight line and substantially parallel to each other and in a second installed position said fingers curving through an arc of at least 90°; and
   d) a marker located in said hole,
   wherein each said spaced arm includes a transition section adjacent a said respective finger, said transition sections of said spaced arms have surfaces spaced from and facing each other, and said surfaces of said transitions sections and said engagement shoulders are sized and shaped to engage each other.

14. A surgical clip according to claim 13, wherein:
said marker is one of a radiographic and MRI-visible marker.

15. A surgical clip, comprising:
   a) a base having spaced engagement shoulders and defining a hole;
   b) two spaced arms extending distally from said base and defining an opening therebetween, said spaced arms having a first width at midportions of said arms;
   c) two fingers extending respectively from said spaced arms, said fingers being of reduced width relative to said first width, and said fingers being offset from each other relative to a longitudinal axis which extends through said base and between said arms, said fingers in a first pre-formed condition extending in a substantially straight line and substantially parallel to each other and in a second installed position said fingers curving through an arc of at least 90°; and
   d) suture material extending through said hole,
   wherein each said spaced arm includes a transition section adjacent a said respective finger, said transition sections of said spaced arms have surfaces spaced from and facing each other, and said surfaces of said transitions sections and said engagement shoulders are sized and shaped to engage each other.

16. A surgical clip, comprising:
   a) a base having spaced engagement shoulders;
   b) two spaced arms extending distally from said base and defining an opening therebetween, said spaced arms having a first width at midportions of said arms; and
   c) two fingers extending respectively from said spaced arms, said fingers being of reduced width relative to said first width, and said fingers being offset from each other relative to a longitudinal axis which extends through said base and between said arms, said fingers in a first pre-formed condition extending in a substantially straight line and substantially parallel to each other and in a second installed position said fingers curving through an arc of at least 90°, wherein each said spaced arm includes a transition section adjacent a said respective finger, said transition sections of said spaced arms have surfaces spaced from and facing each other, said surfaces of said transitions sections and said engagement shoulders are sized and shaped to engage each other, and wherein said arms each include a proximal portion forward said base and a rearwardly extending fin portion spaced radially from a forward end of said proximal portion.

* * * * *